US011559434B2

United States Patent
Bor (10) Patent No.: US 11,559,434 B2
(45) Date of Patent: Jan. 24, 2023

(54) AUTOMATIC CENTRATION OF A SURGICAL PATTERN ON THE APEX OF A CURVED PATIENT INTERFACE

(71) Applicant: AMO Development, LLC, Santa Ana, CA (US)

(72) Inventor: Zsolt Bor, San Clemente, CA (US)

(73) Assignee: AMO Development, LLC, Irvine, CA (US)

( * ) Notice: Subject to any disclaimer, the term of this patent is extended or adjusted under 35 U.S.C. 154(b) by 365 days.

(21) Appl. No.: 16/433,959

(22) Filed: Jun. 6, 2019

(65) Prior Publication Data

US 2019/0282404 A1  Sep. 19, 2019

Related U.S. Application Data

(62) Division of application No. 14/090,292, filed on Nov. 26, 2013, now Pat. No. 10,314,745.

(60) Provisional application No. 61/732,020, filed on Nov. 30, 2012.

(51) Int. Cl.
*A61F 9/008* (2006.01)
*A61F 9/009* (2006.01)

(52) U.S. Cl.
CPC .......... *A61F 9/00825* (2013.01); *A61F 9/009* (2013.01)

(58) Field of Classification Search
CPC .............................. A61F 9/00825; A61F 9/009
USPC .......................................................... 606/4–5
See application file for complete search history.

(56) References Cited

U.S. PATENT DOCUMENTS

| | | | |
|---|---|---|---|
| 2003/0105457 A1 | 6/2003 | Mrochen et al. | |
| 2007/0173791 A1* | 7/2007 | Raksi | A61F 9/009 606/4 |
| 2007/0293851 A1 | 12/2007 | Muhlhoff et al. | |
| 2008/0078752 A1* | 4/2008 | Bischoff | B23K 26/032 219/121.72 |
| 2013/0041354 A1* | 2/2013 | Brownell | A61F 9/00836 606/4 |

* cited by examiner

*Primary Examiner* — Aaron F Roane
(74) *Attorney, Agent, or Firm* — Johnson & Johnson Surgical Vision, Inc.

(57) ABSTRACT

An apparatus to treat a patient comprises a laser beam, a measurement module, a scanner and a curved patient interface lens. The curved patient interface is measured with a pattern so as to determine a plurality of distances of the curved surface at a plurality of measurement locations. The measurement pattern may comprise the plurality of measurement locations distributed about a central measurement axis corresponding to the laser treatment axis. The plurality of measurement locations of the curved surface may correspond to a portion of a planned treatment profile, such that the measured distances correspond to alignment of the planned treatment. The plurality of distances can be used to determine an apex of the curved surface of the patient interface and to align the laser treatment axis with the apex of the curved surface.

20 Claims, 7 Drawing Sheets

FIG. 8

AUTOMATIC CENTRATION OF A SURGICAL PATTERN ON THE APEX OF A CURVED PATIENT INTERFACE

CROSS-REFERENCE TO RELATED APPLICATIONS

This application is a divisional of and claims priority to U.S. patent application Ser. No. 14/090,292, filed Nov. 26, 2013, which claims the benefit of priority to U.S. Provisional Application Ser. No. 61/732,020, filed Nov. 30, 2012, all of which are incorporated herein in their entirety.

BACKGROUND

The present disclosure is generally directed to methods and apparatus to treat an eye with a laser beam, including aligning a laser treatment with the eye. Although specific reference is made to centration of a surgical pattern on the apex of a curved patient interface, the methods and apparatus as described herein can be used in many applications in which a laser is used to treat material.

The eye is used for vision and has several tissues that allow a person to see. The cornea and lens of the eye form an image on the retina where the image is sensed. The refractive properties of the eye can be such that the image formed on the retina is less than ideal. For example, the eye may have less than ideal vision resulting from one or more refractive causes such as nearsightedness, far sightedness, and astigmatism.

Although many prior technologies have been proposed and used to correct vision of the eye, many of these prior technologies may provide less than ideal results in at least some instances. For example, with spectacles and contact lenses, a corrective lens is placed in front of the eye or on the cornea to improve the image formed on the retina. However, not all patients tolerate spectacles and contact lenses and these corrective lenses are only effective when worn by the patient. Also, spectacles and contact lenses may provide less than ideal correction of higher order aberrations of the eye such as spherical aberration and coma. Surgical treatments have been proposed and developed such as radial keratotomy (hereinafter "RK"), photorefractive keratectomy (hereinafter "PRK") and laser assisted in situ keratomileusis (hereinafter "LASIK"). With RK, cuts may be made deep into the cornea, and although these cuts can provide an initial correction of vision, long term stability of RK treated eyes may be less than ideal in at least some instances. With PRK, healing of a layer of epithelium, which is removed for treatment, can take longer than would be ideal and may result in discomfort to the patient while the epithelium regenerates. Although LASIK can provide faster healing of the eye than PRK, in at least some instances cutting of the LASIK flap can be less than ideal, and applanation of the eye with a microkeratome may result in a temporary increase in intra-ocular pressure.

Laser surgery with ultra-short pulse lasers such as femtosecond lasers have been used to treat the eye. These pulsed lasers can make very accurate incisions of the eye and can be used in many ways to treat the eye. For example, short pulse lasers can be used to incise corneal tissue to make flaps with Femto-LASIK. Additional types of incisions that can be performed with the short pulse lasers include incisions for paracentesis, limbal relaxing incisions, and refractive incisions to shape the cornea, for example. The surgical incisions formed with ultra-short pulsed lasers can be quite accurate, and in at least some instances it can be helpful to hold the eye in position with a patient interface that couples the laser to the incised tissue of the eye such as the cornea. The patient interface can hold the eye in place so that an incision can be formed at the correct depth in the cornea. Prior patient interfaces have included a flat surface to contact the cornea. Although effective in facilitating cutting tissue at the intended depth, the flat patient interface may deflect the cornea more than would be ideal and provide less than ideal coupling to the cornea in at least some instances.

Although a patient interface with a curved surface to contact the cornea has been proposed, the prior methods and apparatus can provide less than ideal results in at least some instances. At least some of the prior treatments may result in an incision that is too deep, not deep enough, or both, in at least some instances. Curved patient interfaces can be difficult to align with the laser treatment and difficult to manufacture to within the tolerances of laser eye surgery. The alignment tolerances of the prior laser eye surgery systems may be less than ideally suited for use with a curved patient interface. In at least some instances, one or more components of the prior laser system can drift or move after alignment which can affect the accuracy of the placement of the cut profile, and the central treatment axis of the prior laser eye surgery systems may be difficult to define to within the tolerances appropriate for use with a curved patient interface.

In light of the above, it would be helpful to provide improved methods and apparatus to treat tissue. Ideally such methods and apparatus would overcome at least some of the above mentioned deficiencies of the prior methods and apparatus, for example by providing more accurate cutting of tissue without substantial deflection of corneal tissue and in a manner that can be used to treat many patients.

SUMMARY

Embodiments disclosed herein provide improved methods and apparatus to treat an eye of a patient. A laser source configured to generate a treatment beam is coupled to a measurement module and a processor. A curved patient interface lens can be placed in a loading deck prior to treatment. The processor comprises instructions to measure the curved patient interface with a measurement pattern so as to determine a plurality of distances of the curved surface at a plurality of measurement locations. The plurality of distances at the plurality of measurement locations can be measured rapidly, and the laser system can be adjusted to the curved patient interface based on the plurality of distances. The treatment profile can be aligned with the patient interface so as to decrease differences among the measured distances, which can significantly decrease cut depth errors of the treatment profile. The measurement pattern may comprise the plurality of measurement locations distributed about a central measurement axis, and the central measurement axis may correspond to the laser treatment axis. The plurality of distances can be used to determine an apex of the curved surface of the patient interface and to align the laser treatment axis with the apex of the curved surface. The processor may comprise instructions to measure the plurality of distances and to automatically align the laser treatment axis with the apex of the patient interface based on differences among the plurality of distances when the curved lens has been placed in the loading deck. Adjusting the location of one or more of the laser treatment axis, the laser treatment profile, the measurement axis or the plurality of measurement locations based on the plurality of distances can substantially inhibit errors associated with manufacturing tolerances of the loading deck, the curved lens and the treatment axis of the laser system.

The plurality of measurement locations of the curved surface may correspond to a portion of a planned treatment profile, such that the measured distances correspond to alignment of the planned treatment. The portion of the planned treatment profile may comprise an outer portion planned to extend to a surface of the cornea, such that the measured distances correspond to alignment of the outer portion of the treatment profile configured to extend to the surface of the cornea. The plurality of distances corresponding to locations and alignment of the planned treatment allow subtle errors to be detected, and can permit rapid and accurate adjustment to one or more of the laser treatment axis, the treatment profile, the central measurement axis or the measurement locations. The differences among the plurality of distances can be compared to determine a minimum distance and a maximum distance of the curved surface, and the laser system can be adjusted based on a difference between the maximum and the minimum. The angle of the adjustment can be determined independently of the radius of curvature such that one or more of the laser treatment axis, the treatment profile, the central measurement axis, or the measurement locations can be accurately adjusted toward the apex of the curved surface independently of the radius of curvature of the curved surface. The radius of curvature of the curved surface or an approximate radius of curvature can be used to determine the amount of the adjustment toward the apex. The amount of adjustment and the angle of the adjustment may comprise components of a vector extending between the measurement axis and the apex of the curved surface. A tilt angle of the curved surface can be determined based on the maximum and the minimum, and the treatment profile moved toward an apex of the patient interface based on the tilt angle. The plurality of measurement locations can be distributed about the central measurement axis, and the tilt angle may comprise an angle of the central axis. The laser treatment axis may be decentered based on the angle to align the treatment with the curved surface and substantially decrease cut depth errors of the incision.

In a first aspect, embodiments provide an apparatus to treat an eye having a cornea. A laser source is configured to generate a laser beam to treat the eye. An optically transmissive interface is configured to couple to the cornea of the patient, in which the optically transmissive interface has a curved surface to contact an anterior surface of the cornea. An optical delivery system is configured to deliver the laser beam to the eye. A measurement module is coupled to the optical delivery system to measure the curved surface. A processor comprises computer readable instructions, and the processor is coupled to the optical delivery system and the laser source to treat the cornea with a treatment profile. The computer readable medium comprises instructions to measure a plurality of distances of the curved surface at a plurality of locations and to align the treatment profile with the curved surface based on the plurality of distances.

In many embodiments, the computer readable memory comprises instructions to adjust a location of the treatment profile based on differences among the plurality of distances.

In many embodiments, the computer readable memory comprises instructions to decenter the treatment profile or a central treatment axis to decrease the angle.

In many embodiments, the computer readable memory comprises instructions to define a central treatment axis of the optical delivery system based on the plurality of distances.

In many embodiments, the computer readable memory comprises instructions to move a central location of the treatment profile toward an apex of the curved surface based on the plurality of distances.

In many embodiments, the computer readable medium comprises instructions to determine a tilt angle of the curved surface at the plurality of locations and to adjust a center position of a laser treatment beam based on the tilt angle. The plurality of locations may comprise a central location and the curved surface may comprise an apex. The tilt angle may comprise a tilt angle of the central location, and the center position can be adjusted toward the apex based on the tilt angle of the central location.

In another aspect, embodiments provide a method of treating a patient having a cornea. An optically transmissive interface is provided to couple to the cornea of the patient. The optically transmissive interface has a curved surface to contact an anterior surface of the cornea. A plurality of distances of the curved surface is measured at a plurality of locations with a light beam. A location of the treatment profile is adjusted based on differences among the plurality of distances to align the treatment profile with the curved surface.

In many embodiments, adjusting comprises decentering the treatment profile or a central axis of the laser treatment to decrease the angle.

In many embodiments, a central location of the treatment profile comprising a central treatment axis is moved toward an apex of the curved surface based on the plurality of distances.

In many embodiments, a tilt angle of the curved surface at the plurality of locations is determined, and a central treatment axis of a laser treatment beam is adjusted based on the tilt angle. The plurality of locations may define a central location along a measurement axis and the curved surface may comprise an apex. The tilt angle may comprise a tilt angle of the central location, and the measurement axis can be adjusted toward the apex based on the tilt angle.

In many embodiments, an elevation difference among the plurality of distances is determined and a location of the treatment profile is adjusted based on the elevation difference so as to decrease the elevation difference and align the treatment profile with the curved surface. An angle of the curved surface may be determined based on the elevation difference and the location of the treatment profile is adjusted based on the angle to decrease the elevation difference. The plurality of locations can be positioned about a central measurement axis, and the central measurement axis can be offset from a first location to a second location to decrease the angle.

In many embodiments, the plurality of distances at the plurality of locations corresponds to a portion of a treatment profile of the cornea.

In many embodiments, the treatment profile comprises an outer boundary and the plurality of locations of the treatment profile correspond to pulses at the outer boundary of the treatment profile in order to align the outer boundary of the treatment profile with the curved surface.

In many embodiments, the plurality of locations of the curved surface corresponds to a plurality of locations of pulses of the treatment profile within an epithelial layer of the cornea.

In many embodiments, the light beam comprises a laser beam, and the laser beam comprises a treatment beam having a second energy per pulse and a measurement beam having a first energy per pulse, the first energy per pulse less than the second energy per pulse and less than a threshold of optical breakdown.

In many embodiments, the light beam comprises one or more of infrared light, ultraviolet light, or visible light.

Additional aspects of the present disclosure are recited in the claims below, and can provide additional summary in accordance with embodiments. It is contemplated that the embodiments as described herein and recited in the claims may be combined in many ways, and any one or more of the elements recited in the claims can be combined with any other of the elements recited in the claims in accordance with embodiments of the present disclosure and teachings as described herein.

DETAILED DESCRIPTION

The embodiments as described herein can be beneficially combined in many ways to provide improved alignment of a laser treatment with a curved surface. The curved surface can be a curved tissue surface, such as a tissue of the eye. The embodiments described herein can be combined with one or more of many surgical procedures to provide an improved surgical result, and can be used to correct errors in alignment attributable to one or more of many sources.

The embodiments as described herein can be particularly well suited to decrease decentration and depth error for incisions that can be sensitive to alignment errors, such as incisions for LASIK flaps, all-laser LASIK, Femto-LASIK, IntraLASIK, or iLASIK, Intralase Enabled Keratoplasty (hereinafter "IEK"), arcuate incisions such as with autologous keratoplasty (hereinafter "AK"), limbal relaxing incisions (hereinafter "LRI"), clear corneal incisions (hereinafter "CCI") and paracentesis procedures, for example. The embodiments as described herein are well suited for treatments of the lens such as capsulorhexis, for example. In many embodiments, the decentration error and corresponding depth error can be substantially eliminated. The alignment procedure can be readily performed before the surgical procedure so as to provide the beneficial alignment and cutting as described herein. For example, the alignment procedure can be performed with a single use patient interface lens placed in the loading deck before the eye of the patient is treated.

The embodiments as described herein can be used to provide accurate incisions with a patient interface having a curved surface to contact the eye. The patient interface can be accurately aligned before each procedure, so to increase the centration tolerances of the components of the patient interface such as the lens holder and the lens, and so as to increase the cone length tolerance of the focusing optics that provide optical breakdown at a depth in the tissue, for example.

The methods and apparatus as described herein have the advantage of measuring the lower curved patient interface, and rapidly and automatically aligning the treatment with the lower curved surface. The lower curved surface that contacts the patient can be measured at a plurality of locations, and the placement of the procedure adjusted automatically prior to treatment based on the measurements of the lower curved surface. The measured plurality of locations may correspond substantially to locations of the treatment profile, such that the measured errors correspond substantially to errors of the planned treatment profile. For example, the measured plurality of locations may correspond to an outer boundary of the treatment profile intended to extend substantially from the stroma through the epithelial layer to the curved surface of the patient interface. The centration of the treatment can be adjusted based on the measured plurality of locations such that the outer portion of the treatment profile can be accurately aligned.

While many measurement beams can be used, in many embodiments the surgical laser beam is used to measure and detect position error of the apex of the curved surface of the patient interface relative to a planned position of the treatment. This position error can be an x and y error that can be fed back to the software to update the zero position of the scanning galvanometers (hereinafter "galvos"). The cylindrical side cut and the axis of the curved dome shaped surface to contact the cornea can be precisely aligned and the depth error of the side cut incision can be minimized. The side cut incision may comprise one or more of many known incisions, such as arcuate incisions, IEK, or corneal incision for cataract surgery, for example.

The surgical laser beam can be used to measure the z position (i.e. depth position) of the apex of the curved patient interface, and z position may be measured together with the x and y position errors of the apex. In many embodiments, the X, Y, and Z position errors can be measured together, for example determined simultaneously based on measurements of positions of the lower curved surface shaped to contact the cornea. The position errors can be fed back to the system to improve alignment. For example, the $\Delta Z$ error of the apex can be fed back to the software driving the Z position of the incision at the focal point, such that the depth error caused by the manufacturing inconsistency of the cone length of the focusing optic can be compensated. Transverse $\Delta X$ and $\Delta Y$ errors associated with the slow drift of the scanning galvo system or of the surgical microscope can be substantially eliminated based on feedback of the measured positions of the curved surface shaped to contact the cornea of the patient.

Figure 1:
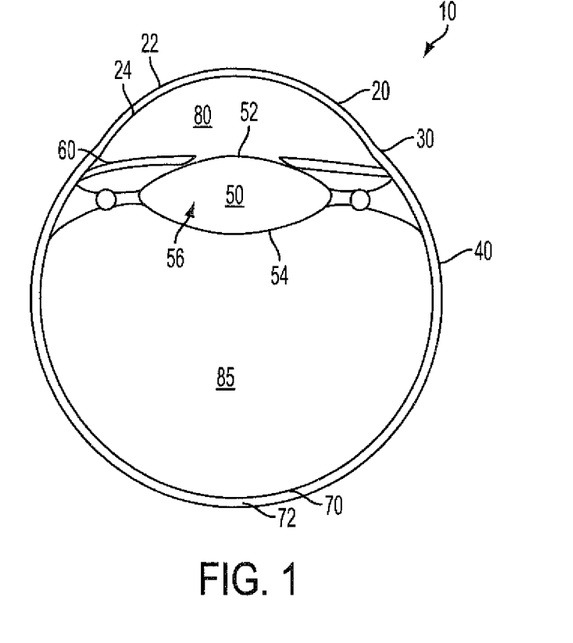
FIG. 1 shows an eye suitable for treatment, in accordance with embodiments.

FIG. 1 shows an eye 10 suitable for treatment. The eye 10 comprises a cornea 20 and a lens 50, which form an image on the retina 70. The eye 10 is oriented in the patient such that the cornea 20 is located anteriorly and the retina 70 is located posteriorly. The cornea 20 comprises an anterior surface 22 and a posterior surface 24. The cornea 20 is bounded on the periphery by a limbus 30. The anterior surface 22 comprises a curved surface to refract light at the air cornea interface. An aqueous humor 80 is located between posterior surface 24 and lens 50. Lens 50 comprises an anterior capsule 52, a posterior capsule 54, and a nucleus 56. A vitreous humor 85 is located between the lens 50 and retina 70. The retina 70 comprises a fovea 72 for high visual acuity.

Figure 2:
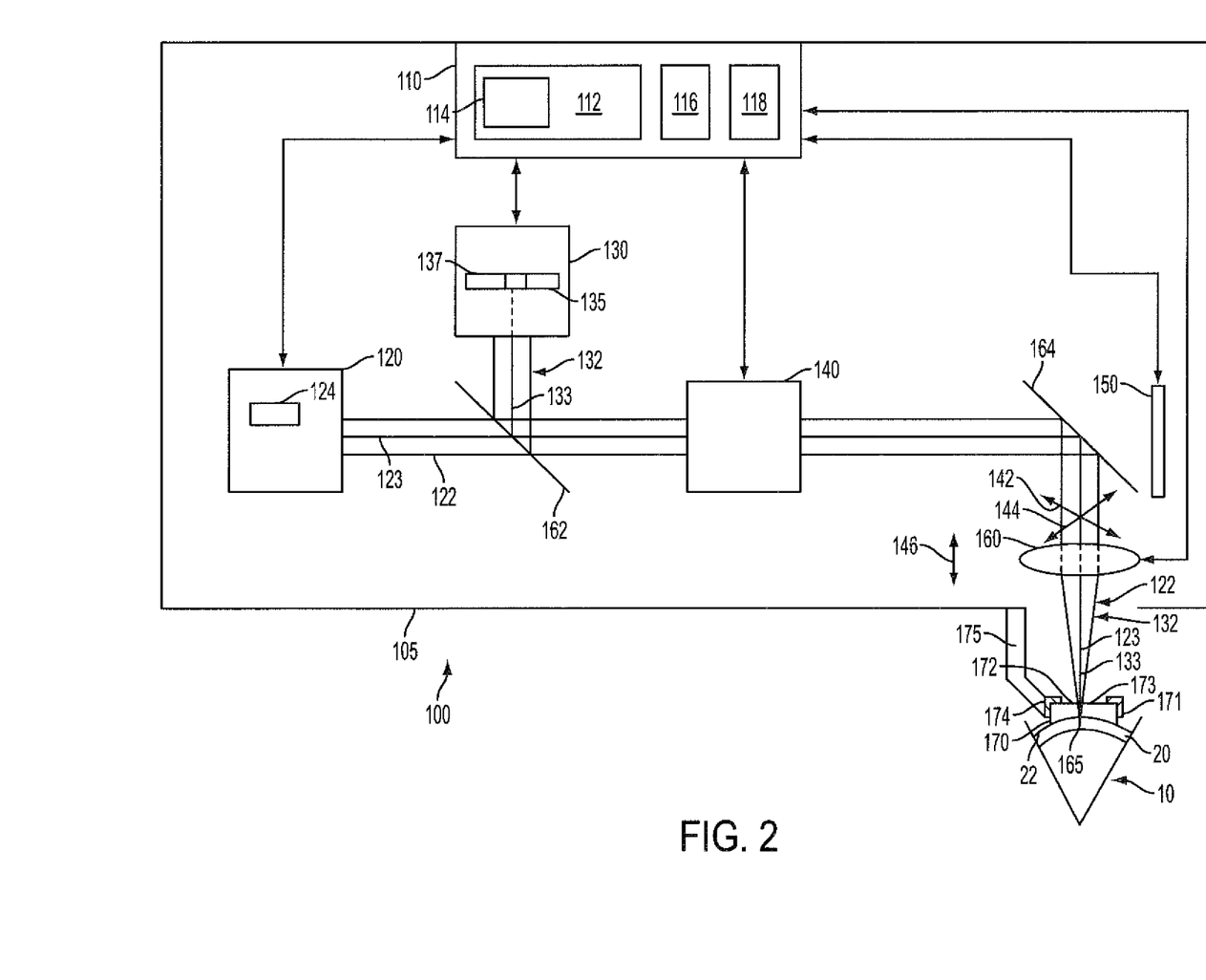
FIG. 2 shows a laser treatment apparatus having a measurement module, in accordance with embodiments.

FIG. 2 shows a laser treatment apparatus 100. The laser treatment apparatus 100 comprises a chassis 105, which supports many of the components as described herein. The laser treatment apparatus 100 comprises a controller 110 to control the components of the laser treatment apparatus. A laser source 120 generates a laser beam 122 to treat the eye. The laser beam 122 comprises one or more of infrared light, ultraviolet light, or visible light. The laser beam 122 extends along an axis 123. A measurement module 130 is configured to receive a light from a measurement path 132 to measure the position of one or more of the patient interface, or a location of a tissue structure of the eye, such as a surface of the cornea, a surface of the limbus, or a surface of the lens. The measurement path 132 extends along an axis 133. The light traveling along measurement path 132 may comprise one or more of infrared light, ultraviolet light, or visible light. A beam splitter 162 is configured to align the treatment beam 122 with the measurement path 132. The light transmitted along the measurement path 132 may comprise a portion of the laser beam reflected from the patient interface or tissue structure of the eye, or a light reflected from a separate light source such as an OCT scanner as described herein. A scanner module 140 is configured to deflect the treatment beam. The scanner module 140 may comprise a pair of mirrors coupled to galvanometers, for example. A focusing optic 160 is configured to adjust the focus of the laser beam 122 to a focal point 165 at a target depth within the tissue of the eye. The scanner module 140 and the focusing optic 160 may comprise components of an optical delivery system to deliver the treatment beam to the eye. The focusing optic 160 may comprise a variable focal length lens, a movable lens, and combinations thereof, for example, and may be coupled to a third galvo. A beam splitter 164 is configured to deflect a majority of the laser beam toward the focusing optics 160 and to pass a portion the laser beam toward a detector 150. A patient interface 170 is configured to optically couple the eye to the laser treatment apparatus and to hold the eye in place with mechanical coupling of the eye to the laser treatment apparatus.

The controller 100 comprises a processor 112, a computer readable memory 114 and a display 116 and a communication module 118. The controller 110 comprising the communication module 118 is coupled to the laser source 120, the measurement module 130, and the optical delivery system comprising the scanner module 140 and the focusing optic 160 so as to provide three-dimensional (hereinafter "3D") scanning of the focal point 165 in the tissue of the eye. The 3D cut profile can be configured in one or more of many ways to provide a desired therapeutic effect.

The controller 110 may comprise a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included, and processors having a plurality of processing units (or even separate computers) may be employed in a wide range of centralized or distributed data processing architectures. The computer readable memory may comprise one or more of random access memory (hereinafter "RAM"), read only memory (hereinafter "ROM"), compact disk read only memory (hereinafter CD-ROM), programmable read only memory (hereinafter "PROM"), erasable programmable read only memory (hereinafter "EPROM"), electrically erasable programmable read only memory (hereinafter "EEPROM"), and many additional known forms of tangible media and computer readable memory. The display 116 may comprise a touch screen display for the user to input data, for example. The communication module may comprise wired and wireless communication circuitry such as serial and parallel communication. The controller 22 can be configured to perform the calculations and signal transmission steps described herein at least in part by programming the controller with the software code, which may be written as a single program, a series of separate subroutines or related programs, for example. The controller 110 may include standard or proprietary digital and/or analog signal processing hardware, software, and/or firmware, and will typically have sufficient processing power to perform the calculations described herein during treatment of the patient.

The laser source 120 to generate the laser beam 122 may comprise a pulse duration and energy so as to provide optical breakdown at a target depth in the material to be processed such as a tissue, for example a tissue of the eye as described herein. The irradiance to induce optical breakdown can be about two hundred gigawatts per square centimeter (200 $GW/cm^2$) or less, for example. The laser source 120 may comprise a laser energy detector and controller 124 to set the laser energy. Non-ultraviolet (UV), ultra-short pulsed laser technology can produce pulsed laser beams having pulse durations measured in femtoseconds, for example. The pulsed laser beam may comprise pulse durations of approximately 50 picoseconds or less, and may comprise pulse durations of at least about 10 femtoseconds, for example. Many types of ultra-short pulsed laser technology may be used for intrastromal optical breakdown. A non-UV, ultra-short (e.g., femtosecond pulse duration), pulsed laser beam can propagate through corneal tissue and to focus at a point below the surface of the cornea to photodisrupt the stromal tissue at the focal point with optical breakdown, for example as described in U.S. Pat. No. 5,993,438. A chirped pulse laser amplification system may be used to provide the pulsed laser beam 122 having the pulse duration and energies as described in U.S. Pat. No. RE37585, for example. The pulsed laser beam 122 is preferably linearly polarized, but may be configured in a different polarization state, for example circularly polarized or randomly polarized.

The scanner module 140 and focusing optic 160 can be used to scan the focal point 165 of the laser beam 122 to provide the 3D treatment profile and incision as described herein. The scanner module 140 is configured to scan the laser beam in a first direction 142 and a second direction 144. The focusing optic 160 is configured to scan the focus of the laser beam in a third direction 146. The first direction 142, the second direction 144 and the third direction 146 may comprise X, Y and Z dimensions, respectively, of the scan pattern. The scanner module 140 may comprise galvanometers and mirrors known to those of ordinary skill in the art. The focusing optic 160 may comprise a variable focal length lens, or a movable lens, or a combination thereof. The focusing optic 160 scanner component and laser can be driven by controller 110 to position the focal point at an intended location to provide the cut profile as described herein.

The 3D treatment profile can be arranged in many ways, and the X, Y, and Z dimensions may comprise one or more of many orientations. In many embodiments, the Z-axis is aligned with the anterior to posterior direction of the eye. For example, the patient may be placed in a supine position during surgery such that the Z-axis of depth scanning corresponds to a vertical dimension. Alternatively, the patient may be seated upright at a slit-lamp configuration of the laser system such that the Z-axis depth scanning into the eye corresponds to a horizontal dimension extending along the visual axis of the patient.

The patient interface 170 may comprise at least one arm 175 extending from the chassis 105 to a loading deck structure 171 to receive a contact lens component 173 of the patient interface. The at least one arm 175 may comprise a plurality of arms arranged in a conical configuration, for example. The contact lens component 173 may be replaced for each patient. The contact lens component 173 of the patient interface 170 comprises an air interface surface 172 orientated away from the patient and a curved contact surface 174 oriented toward the patient to contact the cornea 20. The air interface surface 172 is preferably substantially flat. The air interface surface can be flat to within a few wavelengths of light, for example. Alternatively, the air interface surface 172 of the lens component 173 can be curved as shown in FIG. 2D, for example. The air interface surface 172 may comprise an RMS roughness corresponding to the diffraction limit of the laser beam diameter focused through the air interface surface, for example. The curved contact surface 174 comprises a curved surface to decrease pressure to the cornea when the patient interface engages the cornea. The patient interface 170 may comprise a vacuum and other structures appropriate to hold the cornea in contact with the contact surface 174.

The curved contact surface 174 may comprise one or more of many curvatures and may comprise a spherical curvature, for example. The curvature of the contact surface 174 may correspond to an average curvature of a patient population, or a curvature the patient based on a measured curvature of the cornea of the eye to be treated.

Measurement of the plurality of distances at the plurality of locations of the curved surface corresponding to the treatment profile provides can provide accurate alignment of the treatment and laser beam axis without determination of the curvature of the curved surface. The curvature of the contact surface 174 may comprise an unknown or unidentified curvature when the patient is treated for example. In many embodiments, the treatment apparatus 100 can be configured to align the contact surface 174 with the treatment profile based on the plurality of distances as described herein without identifying or determining the curvature of the contact surface 174. The location of the treatment can be adjusted independently of an amount of curvature of the curved surface based on the plurality of distances measured at locations corresponding to the treatment profile, for example, and the treatment profile can be aligned with the curved surface without identifying an amount of curvature or a radius of curvature of the curved surface, for example.

The laser treatment apparatus 100 may comprise components of the iFS Advanced Femtosecond Laser, commercially available from Abbott Medical Optics of Santa Ana, Calif., USA.

The measurement module 130 comprises components to measure the position of the patient interface or a tissue structure of the eye, or combinations thereof. The measurement module 130 can be configured to measure the position of the curved surface of the patient interface based on light energy reflected from the curved surface. The amount of light energy reflected from the curved surface can be determined by a person of ordinary skill in the art and is related to the index of refraction of the curved surface and the index of refraction of the material in contact with the curved surface such as air. The measurement module 130 can also be used to measure a location of a tissue structure of the eye such as an upper surface of the cornea, a lower surface of the cornea, a surface of the limbus or a surface of the lens, and combinations thereof. The measurement module 130 comprises a reference structure 135 to measure the position of the light reflected from patient interface or from the tissue structure. The reference structure 135 may comprise one or more of a sensor array, at least one pixel of a CCD array, a lens, a mirror, an aperture, a pinhole, or an end of an optical fiber, for example. The reference structure may comprise one or more of a mirror or a light transmitting structure of an optical coherence tomography system (hereinafter "OCT"), a pinhole of a confocal measurement system, at least one pixel of the CCD sensor array of the confocal measurement system, or a Z-axis position of the focal point 165, for example. In many embodiments a central portion 137 of the reference structure 135 can be imaged confocally and coaxially with the focal point 165, such measurement of the patient interface surface or tissue structure corresponds to the placement of the laser beam focal point 165. For example, the central portion 137 may comprise a pinhole of a confocal detector, at least one pixel of a CCD array imaged confocally with the laser beam focal point 165, or a light transmitting structure of an OCT system. The light transmitting structure of the OCT system may comprise an aperture of a light source, a pinhole, or an end of an optical fiber, for example.

Figure 2A:
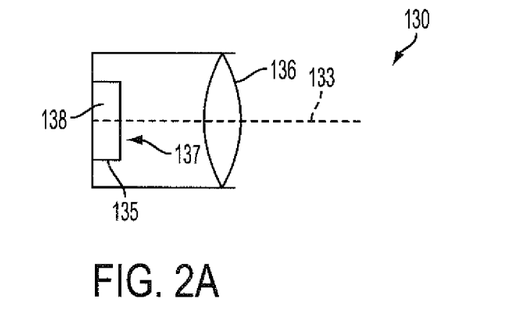
FIG. 2A shows a charge coupled device configuration of the measurement module, in accordance with embodiments.
Figure 2B:
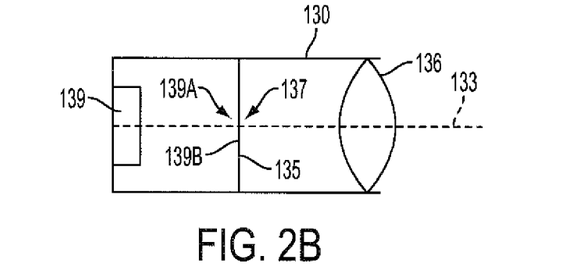
FIG. 2B shows a confocal detector configuration of the measurement module, in accordance with embodiments.

Referring now to FIG. 2A, the charge coupled device (hereinafter "CCD") configuration of the measurement module 130 is shown. The lens 136 focuses light reflected from the surface 174 or the tissue structure as described herein. The reference structure 135 comprises the CCD array 138 and the central portion 137 comprises at least one light sensitive pixel of the CCD array. With the CCD configuration and other configurations as described herein, the energy of laser source 120 can be set below the threshold of optical breakdown with the laser energy controller 124 and the sub-threshold laser beam scanned to determine the position of the surface 174 or the tissue structure as described herein. The CCD sensor array may comprise central pixels, which are sensitive to the light energy of the laser beam of the laser source. The focal point of the laser beam can be imaged onto the CCD sensor array to measure the intensity of the reflected light when the focal point is scanned in three dimensions so as to determine the plurality of distances based on the amount of light energy reflected from the three dimensional positions of the focal point, for example Referring now to FIG. 2B, the confocal detector configuration of the measurement module 130 is shown. The reference structure 135 comprises the light blocking structure 139B and the central portion 137 comprises the aperture 139A formed in the light blocking structure 139B. With the confocal configuration, the energy of laser source 120 can be set below the threshold of optical breakdown with the laser energy controller 124 and the sub-threshold laser beam scanned to determine the position of the surface 174 or the tissue structure as described herein.

Figure 2C:
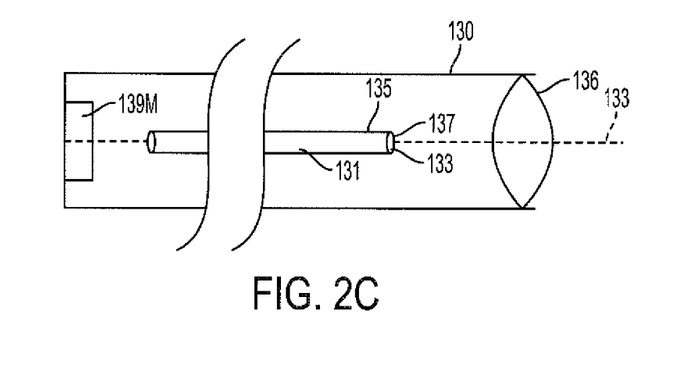
FIG. 2C shows an OCT configuration of the measurement module, in accordance with embodiments.
Figure 2D:
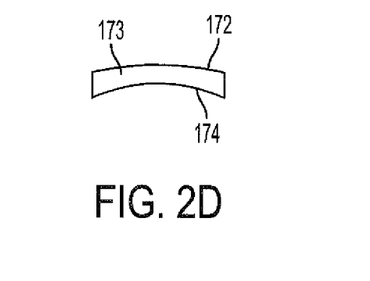
FIG. 2D shows a patient interface lens comprising a curved air interface surface and a curved eye contacting surface, in accordance with embodiments.

Referring now to FIG. 2C, the OCT configuration of the measurement module 130 is shown. The OCT module may comprise one or more components of known interferometer and optical coherence tomography systems such as a movable mirror or prism, one or more reference mirrors, optical fibers and a light source. The light source may comprise one or more of a laser diode, a super luminescent diode, or a laser diode driven sub-threshold, so as to provide a reflected light along the measurement path 132 that is scanned to determine the position of the surface 174 or the tissue structure as described herein. The reference structure 135 may comprise the reference mirror 139M, and the central portion 137 may comprise a central portion of the mirror. The reference mirror 139M may comprise a movable mirror to vary the optical path length or a substantially fixed mirror. Alternatively or in combination, the reference structure 135 may comprise the optical fiber 131, and the central portion 137 may comprise the end 133 of optical fiber 131.

Figure 3:
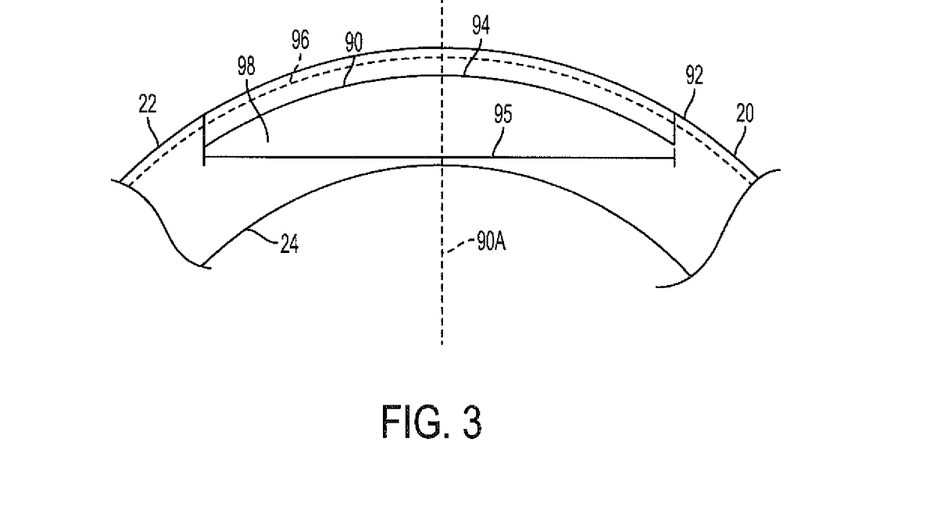
FIG. 3 shows a treated eye, in accordance with embodiments.

Referring now to FIG. 3, an eye 10 is shown treated with the treatment apparatus as described herein. A treatment profile 90 has been formed on the eye, for example cornea 20. The cornea 20 comprises an epithelium 96 and a stroma 98. The treatment profile 90 may comprise a cut profile so as to incise the tissue along the treatment profile 90. The treatment profile 90 comprises an inner portion 94 and an outer edge portion 92. A treatment profile axis 90A can extend through the treatment profile, and the treatment profile can be rotationally symmetric about the treatment profile axis. The treatment profile axis 90A can extend through a central location of the inner portion 94, and the outer edge portion 92 may comprise walls of a cylinder equidistant from treatment profile axis 90A. The inner portion 94 may extend substantially along the stroma 98, and the outer edge portion may extend through a portion of the stroma 98 and through a substantial thickness of the layer of epithelium 96. The outer edge portion 92 may comprise a wall of a cylinder, for example. Alternatively, the outer edge portion 92 may comprise a conic portion, an inverted bevel, an interlocking portion, or other shape to provide a fit of the outer portion with the untreated portion of the cornea. The treatment profile 90 may comprise a known treatment cut profile used to form a flap with LASIK, such as all-laser LASIK, Femto-LASIK, IntraLASIK, or iLASIK, for example. The treatment profile 90 may comprise a treatment profile placed on one or more of many structures of the eye as described herein, and may comprise a surgical incision of one or more of a corneal flap cut, Intralase enabled keratoplasty, autologous keratoplasty, a limbal relaxing incision, a clear corneal incision, a paracentesis or a capsulorhexis, for example.

Figure 4A:
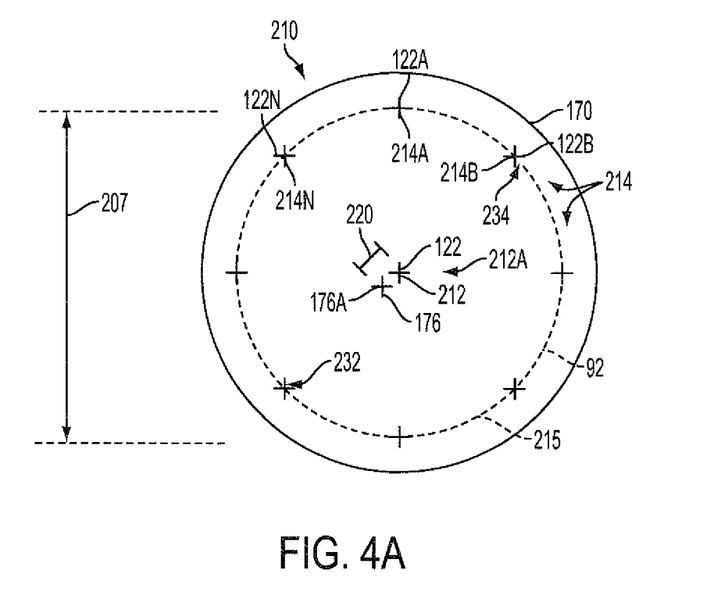
FIG. 4A shows a measurement pattern comprising plurality of positions to align the treatment with the patient interface, in accordance with embodiments.

Referring now to FIG. 4A, a measurement pattern 210 comprises plurality of measurements at a plurality of locations 214 to determine elevation differences and align the treatment with the patient interface. The plurality of locations 214 comprises a first location 214A, a second location 214B, and an Nth location 214N. The plurality of locations 214 can be distributed about a central location 212 located along a central measurement axis 212A. The plurality of measurement locations 214 can be distributed about the central measurement axis 212A so as to define the central measurement axis 212A. The plurality of measurement locations may correspond to positions of the laser beam during treatment to determine whether alignment of the laser beam with the curved contact surface 174 is suitable for treatment. For example, the plurality of locations 214 may comprise positions of the cut profile of laser beam such as the outer portion 92 of the cut profile, which may comprise a circular, oval, elliptical, interlocking, weaved or other profile. The plurality of measurement locations 214 may be arranged on a curved line such as a circle 215 or other geometric shape corresponding to the treatment profile such as an oval, a square, a triangle or an octagon, for example. The plurality of locations 214 located along circle 215 may correspond to locations of a treatment profile having a circular portion contacting the surface of the cornea, for example. Alternatively, the plurality of locations 214 along circle 215 may correspond to locations away from the outer edge portion 92 of the treatment profile, and may be positioned inward or outward from the outer edge portion 92.

The curved contact surface 174 comprises an apex 176, and the measurement pattern 210 can be aligned with the apex to center the treatment. When the circle 215 is not aligned with the apex 176 of the curved contact surface 174, the circle 215 may be tilted along curved contact surface 174, and the circle 215 comprises a maximum height location 232 and a minimum height location 234. The maximum height location 232 corresponds to the maximum height of circle 215 on the curved contact surface 174, and the minimum height location 234 corresponds to the minimum height of the circle 215 on the contact surface 174.

The apparatus 100 and instructions of the processor can be configured such that the central measurement axis 212A comprises the treatment axis 90A, so as to align the treatment axis with the measurement axis. The alignment of the central measurement axis 212A on the apex 176 aligns the treatment axis 90A with the apex 176. The central measurement axis 212A can be defined with the plurality of measurement locations 214 located away from the measurement axis 212A.

The plurality of measurement locations 214 may comprise positions of laser beam 122 distributed about the axis 212A comprising the central location 212. The central location 212 of the scanning measurement pattern 210 can be offset from the apex 176 of curved contact surface 174 of the patient interface 170. The offset from the apex 176 to the central location 212 comprises a decentration error 220. The decentration error 220 can be measured based on the distances of the curved contact surface 174 measured at the plurality of locations 214. The plurality of measurement locations 214 may comprise the first location 214A at a first position 122A of laser beam 122, the second location 214B at a second position 122B of laser beam 122, and the Nth location 214N at an Nth position 122N of laser beam 122. The plurality of measurement locations may comprise at least two positions, for example, and may comprise at least about 20 positions or more, for example. The plurality of measurement locations 214 distributed about the central location 212 may comprise a plurality of locations of the scanning laser beam or a plurality of locations of a scanning low coherence length beam such as an OCT beam as described herein, for example.

Each of the plurality of measurement locations and the apex can be located along a corresponding axis. The apex 176 can be located along an axis 176A, which extends substantially perpendicular to the curved surface at the apex. Each of the measurement locations corresponds to a light path of the measurement beam extending along an axis through the measurement location. For example, an axis of the measurement beam may extend through the first measurement location 214A and may comprise the axis 123 of the laser beam and the axis 133 of the measurement path 132 when the laser beam is positioned at the first location 214A. The measurement beam can be placed at each of the plurality of measurement locations 214 such that the axis of the measurement beam extends through each of the plurality of measurement locations, and the position of the curved surface at the location is measured along the axis of the measurement beam.

Figure 4B:
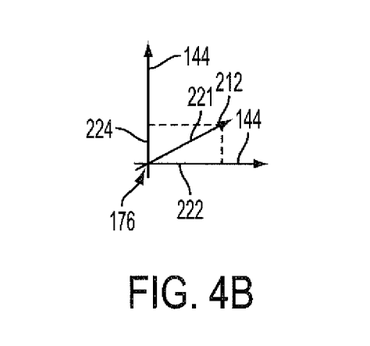
FIG. 4B shows decentration vector of the measurement pattern as in FIG. 4A, in accordance with embodiments.

Referring now to FIG. 4B, a decentration vector 221 is shown extending approximately from the apex 176 of the curved contact surface 174 to the central location 212 of measurement pattern 210. The decentration vector 221 comprises an X component 222 along first direction 142 and a Y component 224 along second direction 144. The decentration vector 221 can be determined based on the plurality of distances of the measurement pattern 210 as described herein.

In many embodiments, however, the measurement pattern 210 can be aligned with the curved contact surface 174 without determining the decentration vector 221. For example, the measurement pattern 210 can be adjusted toward the highest measured elevation of the plurality of locations of the curved surface based on the plurality of distances. The measurement pattern 212 can be adjusted based on the elevation difference between the highest location and the lowest elevation of the plurality of locations, for example. The measurement pattern can be offset based on the plurality of distances at the plurality of locations, and the measurements repeated to determine the alignment.

Figure 5:
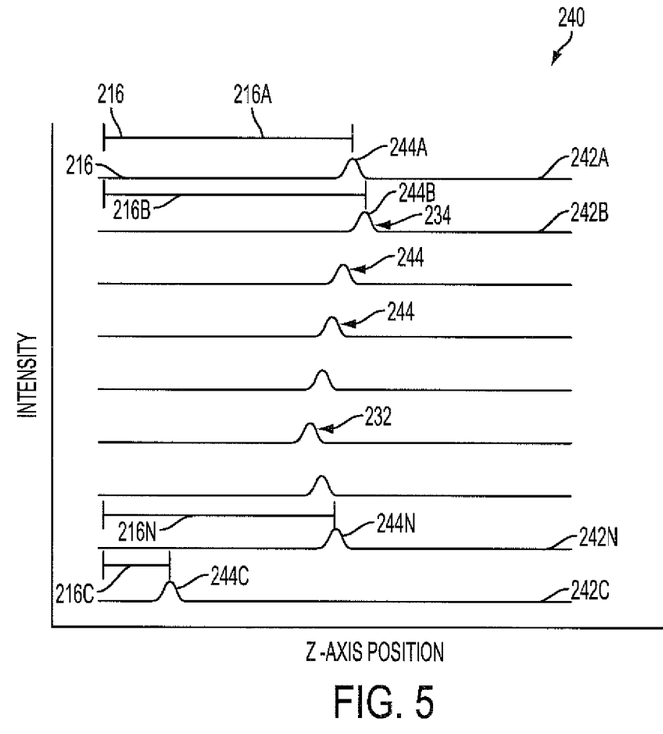
FIG. 5 shows intensities of the light reflected from the patient interface at the plurality of positions along the z-axis of the scan pattern, in accordance with embodiments.

Referring now FIG. 5, a plurality of intensity profiles is shown. The plurality of measured intensity profiles 240 corresponds to the light reflected along the z-axis of the scan pattern at the plurality of positions 214. Each measured intensity profile comprises a peak 244 at the distance of the curved surface 174 along the Z-axis at the X and Y measurement location. A first measured intensity profile 242A corresponds to light measured from the first position 122A as the laser beam focal point 165 is scanned along the Z-axis for a distance, for example a distance of about 4 mm. A second measured intensity profile 242B corresponds to light measured from the second position 122B as the laser beam focal point 165 is scanned along the Z-axis for the distance. An Nth measured intensity profile 242N corresponds to light measured from the Nth position 122N as the laser beam focal point is scanned along the Z-axis for the distance. The first intensity profile 242A, the second intensity profile 242B and the Nth intensity profile comprise first peak 244A, the second peak 244B and the Nth peak 244C, respectively.

The plurality of intensity profiles 240 can be used to determine the position of the curved contact surface 174 for each of the plurality of locations 214. The peak 244 of each intensity profile corresponds to the location of the curved patient contact surface along the third direction 146 comprising the Z-axis. A plurality of distances 216 comprises distances measured along the intensity profiles 240 to the location curved contact surface 174. The plurality of distances 216 comprises a first distance 216A, a second distance 216B, and an Nth distance 216N. Each of the distances corresponds to a height of the curved contact surface 174 along the path of the beam at the measurement location.

The locations of the peaks along the Z-axis can be used to determine the z-axis position of the curved contact surface relative to a reference, and the Z-axis position of the surface can be used to determine the decentration error and corresponding decentration correction.

'The plurality of measurement profiles 240 may comprise a central measured intensity profile 242C corresponding to light measured from the central location 242 of the measurement pattern 210. A central distance 216C can be measured at the central location. The central distance 216C corresponds to the location of the lower surface at the central location 212 of the pattern 210.

The plurality of distances can be referenced to one or more of many structures as described herein. For example, the plurality of distances may correspond to a distance measured from a reference surface such as a plane extending through the center of the measurement pattern. Alternatively or in combination, the plurality of distances can be referenced to a structure of the measurement module or the focusing optics as described herein. In many embodiments, the plurality of distances comprise a plurality of elevations of the lower surface measured at each of the plurality of locations 214, such that the plurality of distances comprise a plurality of heights of the curved contact surface 174 measured at each of the plurality of locations 214.

The plurality of intensity profiles can be measured in many ways in accordance with the teachings described herein. For example, the plurality of intensity profiles may comprise a measured intensity of light on a central portion of a CCD array as described herein. The intensity profile may comprise a measured intensity of light through a pinhole confocal with the laser beam as described herein, or an intensity from an OCT measurement system as described herein, for example.

Figure 6:
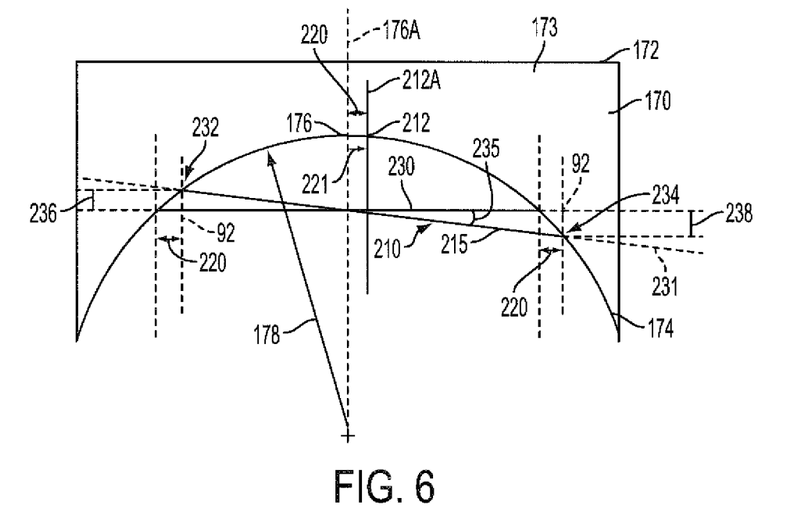
FIG. 6 shows a side cross-sectional view of a measurement pattern corresponding to a laser treatment not aligned with a lower surface of a patient interface lens, in accordance with embodiments.

Referring now to FIG. 6, a side cross-sectional view of measurement pattern 210 is shown which corresponds to laser treatment profile 90. The laser treatment profile is not aligned with the curved contact surface 174 of the contact lens component 173. The measurement pattern 210 is offset from the target location 230 on the lower surface by the decentration error 220 comprising the decentration vector 221. The pattern 210 is offset from the target location 230, such that the locations of measured pattern 210 along the lower surface 174 are sloped at an angle 235. The apex 176 of the lower surface 174 is similarly offset from the central location 212 by the decentration error 220. The positions along the lower surface corresponding to the plurality of measurement locations 214 can be fit to the circle 215, such that circle 215 is tilted at angle 235. The tilted circle 215 comprises a maximum height location 232 and a minimum height location 234. The maximum height location 232 corresponds to the maximum height of circle 215 on the curved contact surface 174, and the minimum height location 234 corresponds to the minimum height of the circle 215 on the contact surface 174. The tilt angle 235 corresponds to the maximum height location 232, the minimum height location 234, and the distance extending therebetween along the direction of the displacement vector 221.

The surface 174 comprises a radius of curvature 178. The surface 174 may comprise a spherical surface to contact the cornea or an aspheric surface to contact the cornea. The radius of curvature may comprise a radius of a spherical curvature, or a radius of an aspheric surface. For example, the radius of curvature 178 may comprise an apical radius of curvature.

The effect of the decentration 220 on the planned treatment can be seen with reference to the outer edge portion 92 of the treatment profile and the curved contact surface 174. A cut depth error 236 corresponds to the outer portion 92 of the treatment profile being located at an increased depth under the curved contact surface 174, which could result in the cut profile not extending to the surface of the cornea and an increased depth of the cut profile, unless corrected. A cut depth error 238 corresponds to the outer portion 92 of the treatment profile being located at a decreased depth, which could result in the cut profile extending into the lens 173 and a depth of the cut profile that may be less than ideal, unless corrected.

The circle 215 comprising the plurality of locations 214 may comprise a circle extending along the curved contact surface 174 when the angle 235 is sufficiently small. When the angle 235 is sufficiently large, the circle 215 may comprise an ellipse when projected on to the curved contact surface 174.

The X component 222 (hereinafter EX) and the Y component 224 (hereinafter EY) of the decentration vector 221 can be determined based on the plurality of measurements of the lower surface. The decentration vector 221 can be determined based on the minimum height 234 (hereinafter "Hmin"), the maximum height 236 (hereinafter "Hmax"), the X and Y locations of the minimum height (hereinafter "Xmin" and "Ymin", respectively), the X and Y locations of the maximum height (hereinafter "Xmax" and "Ymax", respectively), the diameter (hereinafter "D") of the measurement circle 215, and the radius of curvature 178 (hereinafter "R") of the lower curved surface. The following equations can be used to determine EX and EY:

$$EX = R^*(Hmax - Hmin)^*(Xmax - Xmin)/D^2 \text{ and}$$

$$EY = R^*(Hmax - Hmin)^*(Ymax - Ymin)/D^2.$$

Figure 7:
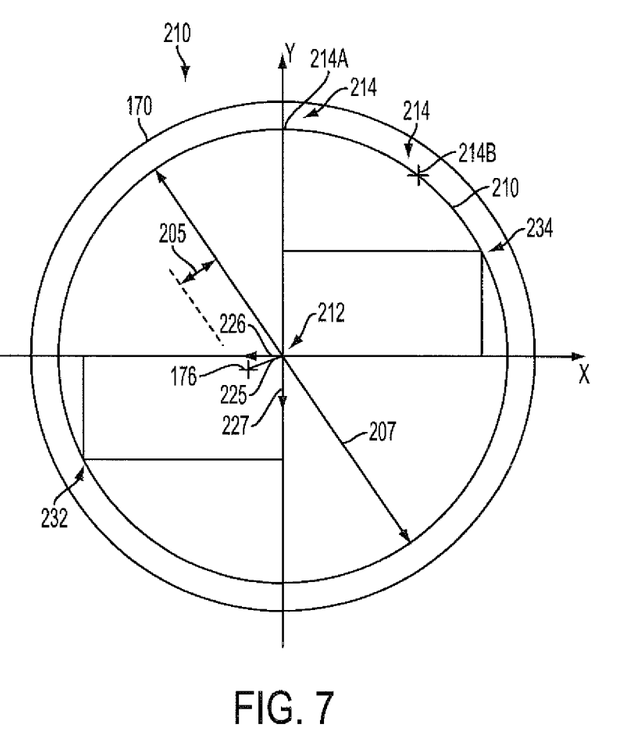
FIG. 7 shows a correction vector capable of decreasing the decentration, in accordance with embodiments.

Referring now to FIG. 7, a correction vector 225 is shown. The correction vector 225 comprises an X-component 226 (hereinafter "DX") and a Y-component 227 (hereinafter "DY"). Movement of measurement pattern in the direction and magnitude of the decentration vector 225 can substantially decrease the alignment error between the curved contact surface and the plurality of locations corresponding to the treatment profile as described herein. The correction vector 225 extends in a direction between the maximum height location 232 and the minimum height location 234. The correction vector can be determined with the following equations:

$$DX = -R^*(Hmax - Hmin)^*(Xmax - Xmin)/D^2 \text{ and}$$

$$DY = -R^*(Hmax - Hmin)^*(Ymax - Ymin)/D^2.$$

The equations described herein are merely provided as examples in accordance with embodiments. For example, alternative equations and approximations may be used as appropriate. The curved surface may comprise an aspheric, or other surface suitable to contact and retain the cornea, for example. Further, an approximate radius of curvature of the lower surface can be used instead of a measured radius of curvature of the lower surface. Also, the values of Hmin, Hmax, Xmin, Xmax, Ymin and Ymax be approximated by identifying the maximum and minimum values from the plurality of distances at the plurality of measurement locations.

In many embodiments, the distances measured at the plurality of measurement locations are constrained to a shape, for example a circle or an ellipse, so as to increase measurement accuracy. For example, the Rayleigh length of the laser beam focused by the fully illuminated objective is about +−9 um, which can be measured with a CCD array as described herein, for example. Based on this Rayleigh length 36 measurement points around the periphery of the scan can provide an accuracy of approximately +/−3 um of the Z measurement.

Figure 8:
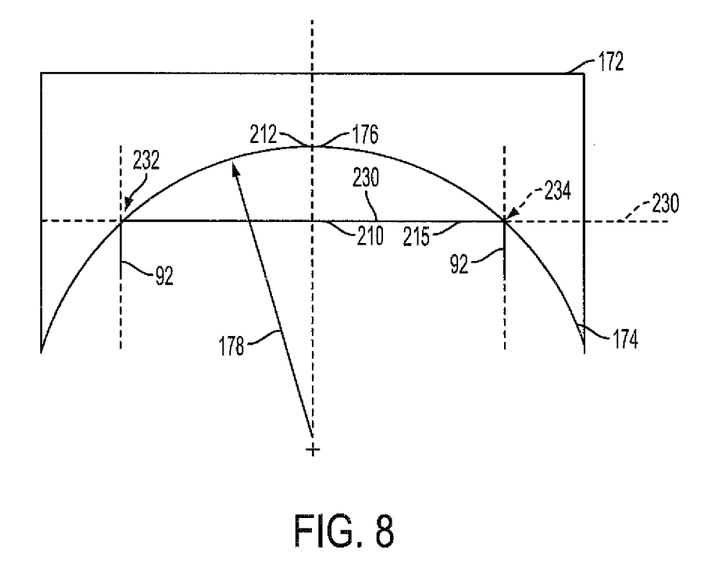
FIG. 8 shows the laser treatment apparatus aligned with the lower surface of the patient interface lens, in accordance with embodiments.

Referring now to FIG. 8, the measurement pattern and the intended laser treatment are shown aligned with the lower surface of the patient interface lens. The measurement pattern 210 is aligned with the target location 230, such that circle 215 extends along the curved contact surface 174 with the cut depth error 236 and the cut depth error 238 substantially inhibited. The outer portion 92 of the treatment profile 90 is aligned with the curved contact surface 174, such that the patient can be treated. The apex 176 is aligned with the central location 212 of the measurement pattern 210.

Referring now to Table 1, a method 900 of treating a patient is shown.

TABLE 1

Method 900 of treating a patient

905- Attach the patient interface with the curved contact lens to the loading deck
910- Z ranging to determine the Z-axis position of the curved surface
915- Fit a circle to the measurement points
920- Determine the minimum height and the maximum height
925- Determine alignment of the scan pattern on the curved surface
930- Determine the tilt angle of the plurality of locations
935- Determine the location of the apex
940- Determine the X and Y components of the decentration vector
950- Determine the decentration correction vector
955- Correct the depth error at the plurality of locations
960- Correct the decentration error
965- Decenter the galvos by □X and □Y
970- Repeat steps until absolute value of Hmax-Hmin becomes small
975- Measure the cone length of the focusing optic
980- Measure the Z-axis distance to the apex of the lower surface
985- System is ready for surgery
990- Curved surface of the interface contacts the cornea of the patient
995- Patient is treated with the laser beam
997- Repeat above steps (other eye, for example)

At a step 905, the patient interface with the curved contact lens is attached to the loading deck.

At a step 910 the Z ranging as described herein is used to measure reflection at a plurality of locations of the curved surface so as to determine the Z-axis position of the curved surface at each of the plurality of locations. Each of the measurements can extend a distance of 3-4 mm along the z-axis. This measurement can provide a high signal to noise ratio since the reflectivity of the glass-air interface has a reflectivity about 2 orders of magnitude higher than the reflectivity of the $3^{rd}$ Purkinje image. At least about 36 measurement frames can be measured per revolution of the scan, for example.

At a step 915 a circle is fit to the measurement points. If the apex is decentered with respect to the center of the scan pattern the circle will have a tilt as described herein.

At a step 920, the minimum height of the scan pattern at the minimum height location is determined and the maximum height of the scan pattern at the maximum height location is determined. In many embodiments the minimum height and the maximum height are determined from the circle fit to the plurality of distances as described herein. Alternatively, the minimum height and the maximum height of the scan pattern can be determined directly from the elevations of the curved surface at the plurality of locations, for example when the measurements are sufficiently accurate.

At a step 925, alignment of the scan pattern on the curved surface to contact the patient is determined. The alignment can be determined based on the difference between maximum height and the minimum height, for example. The alignment can be sufficiently accurate when the difference between the maximum height and the minimum height is within a predetermined range, for example within a few microns.

At a step 930, the tilt angle of the plurality of locations can be determined. The tilt angle can be determined based on the difference in elevation between the minimum height and the maximum height and the distance extending therebetween as described herein, for example.

At a step 935, the location of the apex can be determined based on the plurality of measurements of the curved surface at the plurality of locations as described herein.

At a step 940, the X and Y components of the decentration vector 221 are determined as described herein.

At a step 950 the decentration correction vector is determined as described herein.

At a step 955, the depth error at the plurality of locations is corrected based on the plurality of distances measured at the plurality of measurement locations.

At a step 960, the decentration error of the center of the plurality of measurement locations and the center comprising the apex is corrected.

At a step 965, the zero position of the galvos is decentered by $\Delta X$ and $\Delta Y$ At a step 970, one or more of the above steps is repeated. The above steps can be repeated until the absolute value of the Hmax-Hmin number becomes small enough so as to be within a predetermined tolerance, for example a tolerance of about 10 um. The corrected zero positions of the X and Y galvos are accepted and used for treatment when the Hmax-Hmin number has been determined to be within the predetermined tolerance.

At a step 975, the cone length of the focusing optic is measured.

At a step 980, a Z-axis distance to the apex of the lower surface is measured at the accepted and corrected X=0 Y=0 position. The $Z_0$ position of the apex is determined. If the cone has the right length $Z_0$=0. If $Z_0 \neq 0$, this Z-error is corrected based on computer readable software instructions, for example with a command to the Z galvo.

At a step 985, the system is ready for surgery.

At a step 990, the curved surface of the interface contacts the cornea of the patient.

At a step 995, the patient is treated with the laser beam.

At a step 997, the above steps are repeated. For example a new lens can be placed in the loading deck and the laser aligned with the new lens to treat another eye.

It should be appreciated that the method 900 of treating the patient provides non-limiting examples in accordance with embodiments as described herein. A person of ordinary skill in the art will recognize many variations and adaptations based on the teachings described herein. For example, the steps of the method can be performed in a different order, and the steps can be deleted, or added, and may comprise multiple steps or sub-steps based on the teachings described herein. Further, many of the steps of method 900 can be performed with the processor system as described herein and one or more of the steps of the method can be embodied software instructions of a computer program embodied on a computer readable tangible medium of the processor system as described herein.

While the exemplary embodiments have been described in some detail, by way of example and for clarity of understanding, those of skill in the art will recognize that a variety of modifications, adaptations, and changes may be employed. Hence, the scope of the present disclosure shall be limited solely by the appended claims and the equivalents thereof.

What is claimed is:

1. A method of treating a patient having a cornea, the method comprising:
   providing an optically transmissive interface to couple to the cornea of the patient, the optically transmissive interface having a curved surface to contact an anterior surface of the cornea;
   measuring a plurality of distances of the curved surface at a plurality of measurement locations with a light beam, wherein the distances are defined along a depth direction, and each measurement location is defined in two transverse directions perpendicular to the depth direction, wherein for each of the plurality of measurement locations, its location in the two transverse directions is known before the measuring step, and the distance of the curved surface at the measurement location is unknown before the measuring step and is obtained by the measuring step; and
   adjusting a location of a treatment profile based on differences among the plurality of distances to align the treatment profile with the curved surface.

2. The method of claim 1, wherein adjusting comprises decentering the treatment profile or a central treatment axis to decrease a tilt angle of the treatment profile.

3. The method of claim 1, wherein a central location of the treatment profile comprising a central treatment axis is moved toward an apex of the curved surface based on the plurality of distances.

4. The method of claim 1, further comprising determining a tilt angle of the curved surface at the plurality of measurement locations and adjusting a central treatment axis of a laser treatment beam based on the tilt angle.

5. The method of claim 4, wherein the plurality of measurement locations defines a central location along a measurement axis and the curved surface comprises an apex and wherein the tilt angle comprises a tilt angle of the central location and wherein the measurement axis is adjusted toward the apex based on the tilt angle.

6. The method of claim 1, further comprising determining an elevation difference among the plurality of distances and wherein a location of the treatment profile is adjusted based on the elevation difference to decrease the elevation difference and align the treatment profile with the curved surface.

7. The method of claim 6, further comprising determining an angle of the curved surface based on the elevation difference and wherein the location of the treatment profile is adjusted based on the angle to decrease the elevation difference.

8. The method of claim 7, wherein the plurality of measurement locations are positioned about a central measurement axis and wherein the central measurement axis is offset from a first location to a second location to decrease the angle.

9. The method of claim 1, wherein the plurality of distances at the plurality of measurement locations corresponds to a portion of the treatment profile.

10. The method of claim 1, wherein the treatment profile comprises an outer boundary and wherein the plurality of measurement locations correspond to pulses at the outer boundary of the treatment profile in order to align the outer boundary of the treatment profile with the curved surface.

11. The method of claim 1, wherein the plurality of measurement locations corresponds to a plurality of locations of pulses of the treatment profile within an epithelial layer of the cornea.

12. The method of claim 1, wherein the light beam comprises a laser beam, the laser beam comprising a treatment beam having a second energy per pulse and a measurement beam having a first energy per pulse, the first energy per pulse less than the second energy per pulse and less than a threshold of optical breakdown.

13. The method of claim 1, wherein the light beam comprises one or more of infrared light, ultraviolet light, or visible light.

14. A method of treating a patient having a cornea, the method comprising:
- providing an optically transmissive interface to couple to the cornea of the patient, the optically transmissive interface having a curved surface to contact an anterior surface of the cornea;
- measuring a plurality of distances of the curved surface at a plurality of measurement locations with a light beam, wherein the distances are defined along a depth direction, and each measurement location is defined in two transverse directions perpendicular to the depth direction, wherein the measuring step includes, for each of the plurality of measurement locations;
  - scanning a focus of the light beam along the depth direction at the measurement location defined in the two transverse directions;
  - measuring a light intensity profile corresponding to a reflected light intensity while scanning the focus along the depth direction; and
  - determining a distance along the depth direction of a peak in the measured light intensity profile to determine the distance of the curved surface; and
- adjusting a location of a treatment profile based on differences among the plurality of distances to align the treatment profile with the curved surface.

15. The method of claim 14, wherein adjusting comprises decentering the treatment profile or a central treatment axis to decrease a tilt angle of the treatment profile.

16. The method of claim 14, wherein a central location of the treatment profile comprising a central treatment axis is moved toward an apex of the curved surface based on the plurality of distances.

17. The method of claim 14, further comprising determining a tilt angle of the curved surface at the plurality of measurement locations and adjusting a central treatment axis of a laser treatment beam based on the tilt angle.

18. The method of claim 17, wherein the plurality of measurement locations defines a central location along a measurement axis and the curved surface comprises an apex and wherein the tilt angle comprises a tilt angle of the central location and wherein the measurement axis is adjusted toward the apex based on the tilt angle.

19. The method of claim 14, further comprising determining an elevation difference among the plurality of distances and wherein a location of the treatment profile is adjusted based on the elevation difference to decrease the elevation difference and align the treatment profile with the curved surface.

20. The method of claim 19, further comprising determining an angle of the curved surface based on the elevation difference and wherein the location of the treatment profile is adjusted based on the angle to decrease the elevation difference.

* * * * *